United States Patent [19]

Alon

[11] Patent Number: 4,690,146

[45] Date of Patent: Sep. 1, 1987

[54] NEUROMUSCULAR STIMULATING APPARATUS

[75] Inventor: Gad Alon, Rockville, Md.

[73] Assignee: Chattanooga Corporation, Chattanooga, Tenn.

[21] Appl. No.: 745,577

[22] Filed: Jun. 17, 1985

[51] Int. Cl.[4] .............................................. A61N 1/36
[52] U.S. Cl. .................................................. 128/422
[58] Field of Search .............................. 128/421–423, 128/419 R

[56] References Cited

U.S. PATENT DOCUMENTS

| 3,646,940 | 3/1972 | Timm et al. | 128/421 |
|---|---|---|---|
| 3,662,758 | 5/1972 | Glover | 128/419 R |
| 3,897,789 | 8/1975 | Blanchard | 128/422 |
| 3,908,669 | 9/1975 | Man et al. | 128/422 |
| 4,084,595 | 4/1978 | Miller | 128/422 |
| 4,095,602 | 6/1978 | Leveen | 128/422 |
| 4,165,750 | 8/1979 | Aleev et al. | 128/422 |
| 4,177,819 | 12/1979 | Kofsky et al. | 128/422 |
| 4,230,121 | 10/1980 | Stanton | 128/422 |
| 4,243,043 | 1/1981 | Sevastianov et al. | 128/422 |
| 4,392,496 | 7/1983 | Stanton | 128/423 W |
| 4,408,609 | 10/1983 | Axelgaard | 128/421 |
| 4,459,989 | 7/1984 | Borkan | 128/421 |
| 4,528,984 | 7/1985 | Morawetz et al. | 128/421 |

OTHER PUBLICATIONS

Strojnik et al "Programmed Six Channel Electrical Stimulator for Complex Stimulation of Leg Muscles During Walking" IEEE Trans BME vol. BME-26, No. 2, Feb. 1979, pp. 112-116.

Primary Examiner—William E. Kamm
Attorney, Agent, or Firm—Bell, Seltzer, Park & Gibson

[57] ABSTRACT

A portable electrical neuromuscular stimulating apparatus is disclosed. The apparatus comprises a plurality of portable electrical stimulation units, with each unit including at least one pair of electrodes adapted to be placed on the body of the patient. Electrical circuit means are provided that operatively interconnect each of the units so that a pulsed electrical energy signal is supplied to each pair of electrodes as desired, whereby a predetermined amount of therapeutic pulsed electrical energy is delivered to the desired muscle.

11 Claims, 3 Drawing Figures

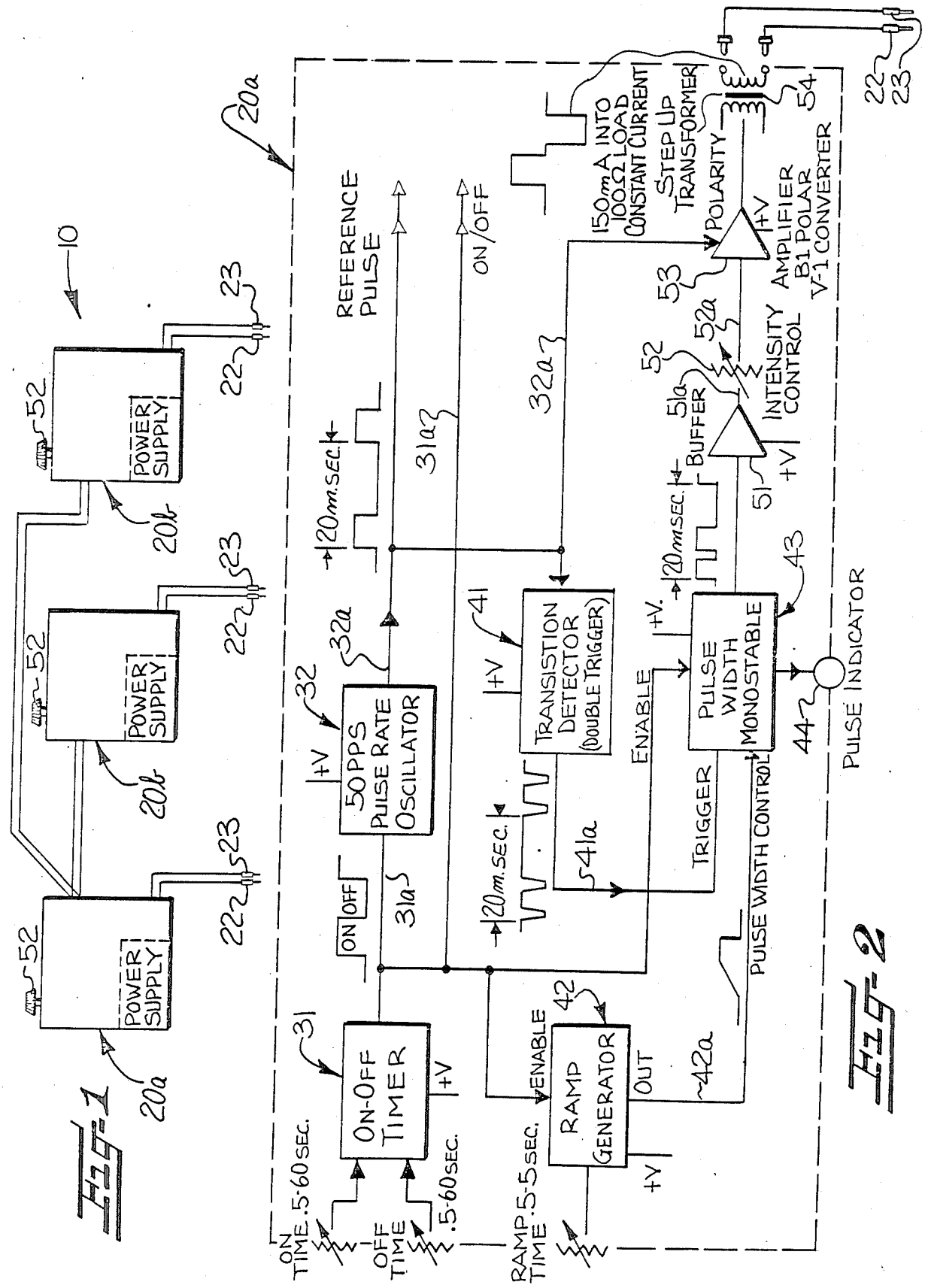

NEUROMUSCULAR STIMULATING APPARATUS

The present invention relates to a portable neuromuscular stimulator which may be employed to control muscle responses and to deaden pain.

Muscle stimulators are well-known in the art, taking various forms and finding general application in the blocking of pain by nerve stimulation and in muscle retraining or re-education. A relatively new use for stimulators is direct and programmed stimulation of muscles with the goal of enabling persons with malfunctioning muscles to more effectively utilize these muscles.

Stimulators have generally been limited to two types. The first being large, non-portable clinical units which are able to support several channels, with each channel comprising a pair of electrodes. This arrangement includes circuitry which is duplicated for each channel and the channels can be operated either synchronously or asynchronously. In addition, these functions can be computer controlled.

Portable stimulator units are now also available. Most of these units have one channel, but some may support multiple channels which are required in many advanced clinical applications, but also contain a significant amount of duplicate circuitry. These units are generally small, and power is supplied by flashlight type batteries, e.g. three penlight or one 9-volt type. These small units discharge batteries quickly if more than one channel is operated since the desired muscle stimulation requires significant amounts of energy in addition to that which is needed to operate the controlling circuitry.

With the foregoing in mind it is an object of the invention to provide a small, easily portable neuromuscular stimulating apparatus having a plurality of channels and which is able to support each channel with adequate power for sustained time periods.

Another object of the invention is to provide a portable multichannel stimulator wherein the channels may be operated either synchronously or asynchronously.

The foregoing objects are accomplished in accordance with the present invention, by providing a portable electrical neuromuscular stimulating apparatus comprising a plurality of interconnected portable electrical stimulation units. Each of the units of the apparatus includes at least one pair of electrodes which is adapted to be placed on the body of the patient. In addition, electrical circuit means operatively interconnect each of the units so that a pulsed electrical current signal is supplied to each pair of electrodes and an effective synchronous or asynchronous stimulation of a desired muscle or a muscle group may be achieved.

BRIEF DESCRIPTION OF THE DRAWINGS

FIG. 1 is a schematic block diagram of an electrical neuromuscular stimulating apparatus which embodies the features of the present invention;

FIG. 2 is a schematic circuit diagram of the circuitry contained in one of the units of the apparatus shown in FIG. 1.

DETAILED DESCRIPTION OF THE ILLUSTRATED EMBODIMENT

Figure 3:
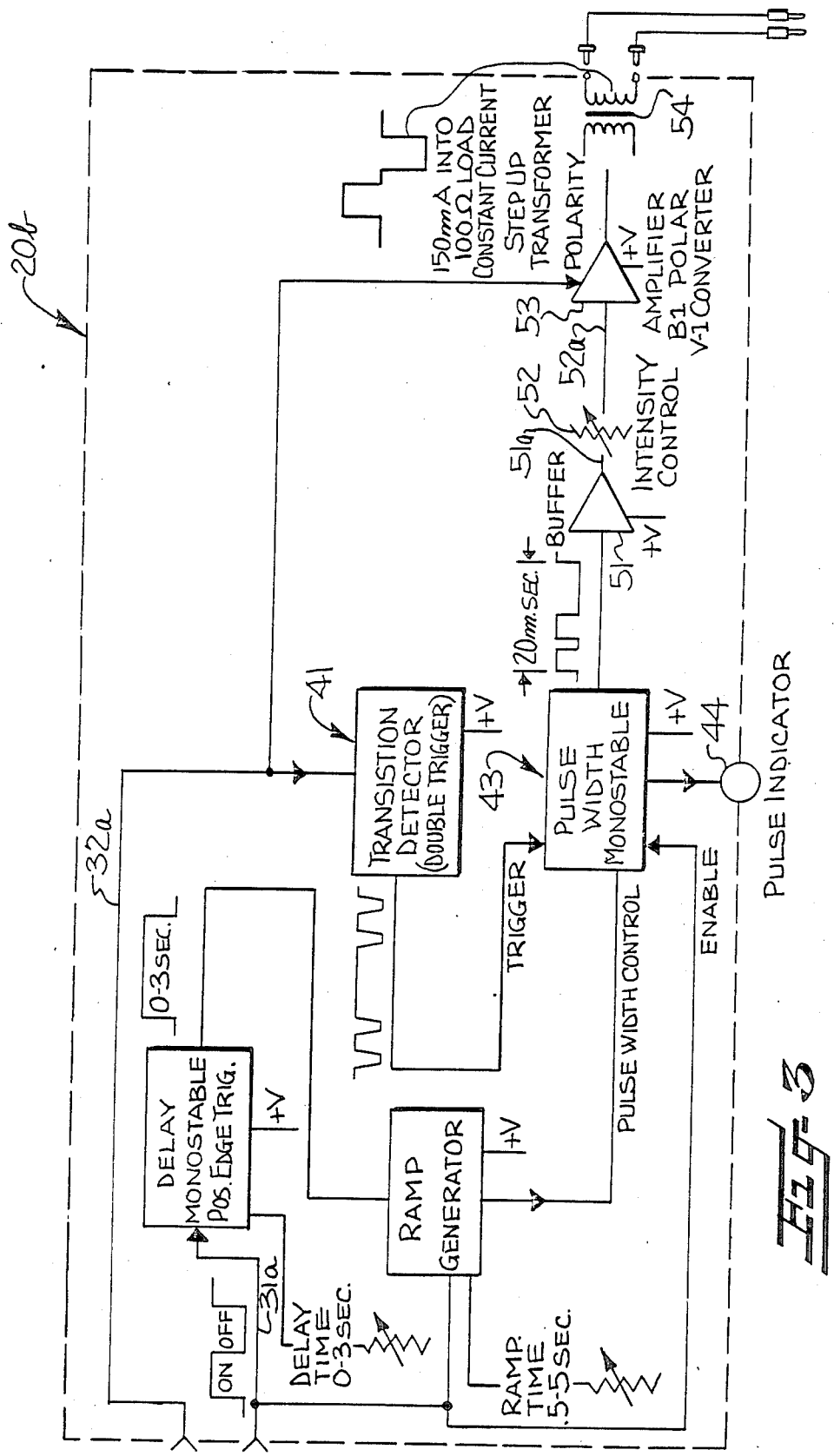
FIG. 3 is a schematic circuit diagram of the circuitry contained in the other units of the apparatus.

While the present invention will be described more fully hereinafter with reference to the accompanying drawings, in which a particular embodiment is shown, it is to be understood at the outset that persons skilled in the art may modify the invention herein described while still achieving the favorable results of this invention. Accordingly, the description which follows is to be understood as a broad teaching disclosure directed to persons of skill in the appropriate arts, and not as limiting upon the present invention.

The description of the invention which follows refers to the accompanying schematic drawings. Detailed reference is made to certain of the manufacturer part numbers, however, all blocks of the diagram referenced herein are well known to electrical circuit designers and detailed discussions thereof are unnecessary. Reference may be made to manufacturer's data books and any one of a number of basic texts on electrical circuit design for further descriptions if desired.

The neuromuscular stimulating apparatus 10 (FIG. 1) of the present invention comprises a plurality of portable units. In the illustrated embodiment, one of the units, which may be designated as the master unit, is indicated at 20a, and two other units, which may be designated as slave units, are indicated at 20b. As will be understood, any number of slave units 20b may be employed with the present invention. Each of units 20a and 20b includes at least one pair of electrodes 22,23, which is adapted to be placed at appropriate locations on the body of the patient. These electrode pairs supply predetermined amounts of therapeutic pulsed electrical energy to the patient, and the electrical circuit means operatively interconnects the units 20a and 20b for supplying a pulsed electrical signal to each pair of electrodes, in the manner further described below.

Referring to FIG. 2, the electrical circuit means includes variable timer means 31 in the master unit 20a, which controls the electrical circuit means to be "on" and "off" at selected time intervals, and as indicated by the square output wave in the output line 31a. The illustrated electrical circuit means is designed so that the "on" time may range from 0.5 to 60 seconds and "off" time may likewise range from 0.5 to 60 seconds. Thus, the user may select the ratio of stimulator "on" time to "off" time by varying the signal output of variable timer means 31.

Also included in the electrical circuit means is oscillator 32 in the unit 20a, which is set to produce an output square wave such as, for example, a wave having a duration of 250 microseconds every 20 milliseconds. The output of oscillator 32 is indicated as a signal in line 32a and is responsive to the output signal of timer means via line 31a, and will be "on" as just described only during the time period when the output of timer means 31 is "on" or "high", thus sending an enable signal to oscillator 32. The output wave of the oscillator 32 on line 32a is a "reference pulse signal" which is delivered to the remaining circuitry of the master unit 20a, as well as to each of the slave units 20b. The aforementioned timer means 31 and oscillator 32 may be found in a single integrated circuit known as an MC-14541 CMOS General Purpose Timer produced by Intersil. Reference may be made to the data sheet covering this device for a detailed explanation of how to produce the aforementioned waveform. Wherever possible, CMOS [Complimetary Metal Oxide Semiconductor] devices should be used to minimize power consumption.

The electrical circuit means of each of the master and slave units 20a, 20b also includes means to modify the reference pulse signal supplied to each unit via line 32a to produce a pulse of modified waveform which forms the input to the associated electrode pair. This modifying means comprises a double trigger transition detector 41, a ramp generator 42 and a pulse width monostable multivibrator 43.

Transition detector 41 receives as an input the oscillator output signal in line 32a and produces an output in line 41a which indicates each transition from a digital "low" state to a digital "high" state; and visa versa. The output signal from the detector 41 in line 41a serves as the trigger input of pulse width monostable multivibrator 43.

The output of transition detector 41 in line 41a is limited by the input of its enable line corresponding to the output signal in line 31a of timer means 31. Thus, a high output of monostable 43 in line 43a necessarily requires timer means 31 to be "on".

Ramp generator 42 is used in this circuit to control the adjustment of the pulse width of the output waveform ultimately delivered to the associated electrode pair and delivered to the patient's muscle. The "ramp time" may be defined as the period of time required for an analog waveform to move from a digital "low" voltage to digital "high" voltage and the time required for this transition is proportional to the slope of the ramp wave form. In this circuit the ramp time is adjustable so that the time period for the ramp to reach the level of a digital "high" state may vary from 0.5 to 5.0 seconds. Thus, when the timer means 31 is on, ramp generator 42 is enabled through the connection to line 31a and the pulse width control in line 42a is operative.

Pulse width monostable 43 is a conventional monostable multivibrator which is used to generate the output wave form or modified wave form in line 43a which is ultimately seen by the patient. Thus, when the "trigger" in line 41a is set, and the ramp in line 42a climbs from a digital "low" state to a digital "high" state, the output of pulse width monostable 43 in line 43a is on or "high" and corresponds to the selected pulse frequency and width as individually set by varying the slope of the ramp in line 42a for each unit 20a, 20b to achieve the maximum effective relationship for stimulation of a particular muscle as determined by the relationship between the master and various slave units. In addition, a pulse indicator light 44 connected to monostable 43 will turn on when the output signal in line 43a is "high", to indicate that electrical energy is being delivered to the electrode pair.

Each of the units 20a, 20b of the stimulator apparatus also includes means comprising a buffer 51, an intensity control 52, an amplifier 53 and a step up transformer 54 for amplifying the modified waveform in line 43a to the proper intensity for muscle stimulation by the electrodes 22,23.

The modified waveform in line 43a passes through the buffer 51 to line 51a, and acts to prevent electrical signals from passing in reverse through the apparatus which could damage the apparatus. The magnitude or intensity of the modified waveform is controlled by intensity control 52 in the form of a variable resistor, which receives the modified waveform in line 51a and which outputs the intensity modified signal in line 52a. An adjustable amplifier 53 is provided which receives as an input the intensity modified waveform in line 52a (mainly a voltage signal) and by adjusting the intensity control 52 by turning the appropriate intensity control knob (see FIG. 1), this signal is transformed into an appropriately amplified current signal of identical shape which is output on line 53a. A Darlington transistor is a device commonly used to amplify current signals and may be used in the present application as the amplifier 53. The current amplified modified waveform is then stepped up via a suitable transformer 54 and forms the input to the muscle stimulating pair of electrodes 22,23.

The slave units 20b receive both the reference signal in line 32a and the timer signal in line 31a from the master unit 20a which facilitates the activation of the various electrode pairs in the desired sequential relationship. The master unit's control of the slave units can alternatively be done by telemetry, including infrared, ultrasonic, and radio frequency methods as known in the art.

Referring to FIG. 3, the electrical circuit means of the slave units 20b further includes a variable time delay means 55 which is operatively associated to each of the slave units 20b in the illustrated embodiment. Each variable time delay means 55 receives the timer signal via line 31a from the master unit 20a and acts to delay the signal so that the electrode pairs of the various units 20a, 20b may be energized in the desired sequence. One well known device suitable for this purpose is the positive edge triggered monostable multivibrator known as a 7556 and manufactured by Motorola Semiconductor Corp. The characteristics of such a device are that the signal exiting the device is identical to the signal entering the device, except for the preselected time delay.

As a further aspect of the present invention, each unit preferably contains its own power supply (note FIG. 1), such as a replaceable 9 volt battery or a rechargeable battery, which substantially increases the portability and reliability of the individual units, and the apparatus as a whole. The power supplies provide the electrical energy required to power the circuitry in each unit, and they also provide the power ultimately delivered by the associated electrode pair.

In the drawings and specification, there has been set forth a preferred embodiment of the invention, and although specific terms are employed, they are used in a generic and descriptive sense only and not for purposes of limitation.

That which is claimed is:

1. A portable electric neuromuscular stimulating apparatus comprising
    a plurality of separate and individually portable electrical stimulation units, with each unit including at least one pair of electrodes adapted to be placed on the body of the patient,
    means mounted in one of said units for generating a reference signal,
    electrical line means for supplying said reference signal to each of said units,
    electrical circuit means mounted in each of said units for adjustably modifying said supplied reference signal and applying the resulting modified signal to the associated electrodes, and
    power supply means mounted in each of said units for powering the associated electrical circuit means.

2. The neuromuscular stimulating apparatus as defined in claim 1 wherein said reference signal generating means includes variable timer means mounted in said one of said units for controlling operation of said electrical circuit means to selected on and off intervals.

3. The neuromuscular stimulation apparatus as defined in claim 2 wherein said electrical circuit means further includes variable time delay means operatively associated with at least each of said units other than said one unit for delaying the application of the on and off intervals to the associated electrodes, and whereby the pairs of electrodes may be energized in a predetermined time sequence.

4. The neuromuscular stimulating apparatus as defined in claim 3 wherein said electrical circuit means further includes means mounted in each of said units for amplifying said resulting modified signal and supplying the amplified signal to the associated electrodes.

5. The neuromuscular stimulating apparatus as defined in claim 4 wherein said power supply means includes battery means mounted in each of said units.

6. A portable electrical neuromuscular stimulating apparatus comprising a plurality of separate and individually portable electrical stimulation units, with each unit including at least one pair of electrodes adapted to be placed on the body of the patient, pulse oscillator means mounted in one of said units for generating a reference pulsed signal of predetermined waveform, electrical line means for supplying the resulting reference pulsed signal to each of said units, and electrical circuit means mounted in each of said units for adjustably modifying the supplied reference pulsed signal to produce a pulsed signal of modified waveform, and including means mounted in each of said units for amplifying the modified pulsed signal and applying the resulting amplified pulsed signal to the associated electrodes.

7. The neuromuscular stimulating apparatus as defined in claim 6 further comprising on-off timer means in said one unit for controlling the output of said pulse oscillator means whereby output pulses of predetermined time intervals are produced.

8. The neuromuscular stimulating apparatus as defined in claim 7 wherein each of said units except said one unit includes variable time delay means for delaying the predetermined time intervals of the received reference pulsed signal and so as to delay the application of the signal to the associated at least one pair of electrodes.

9. The neuromuscular stimulating apparatus as defined in claim 8 wherein said means mounted in each of said units for adjustably modifying the supplied reference pulsed signal comprises transition detector means for detecting each transition of said reference pulsed signal, adjustable ramp generator means, and pulse width generator means operatively connected to said transition means and said ramp generator means for providing said pulsed signal of modified waveform.

10. The neuromuscular stimulating apparatus as defined in claim 9 wherein each of said units further includes pulse indicator means for visually indicating the on intervals of said predetermined time intervals for the associated pair of electrodes.

11. The neuromuscular stimulating apparatus as defined in claim 6 wherein said electrical circuit means further comprises power means in each of said units for powering the same.

* * * * *